(12) United States Patent
Shin et al.

(10) Patent No.: US 11,021,836 B2
(45) Date of Patent: Jun. 1, 2021

(54) CLOTHES-HANDLING APPARATUS

(71) Applicant: LG Electronics Inc., Seoul (KR)

(72) Inventors: Miju Shin, Seoul (KR); Seonglak Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 58 days.

(21) Appl. No.: 16/315,823

(22) PCT Filed: Jul. 6, 2017

(86) PCT No.: PCT/KR2017/007214
§ 371 (c)(1),
(2) Date: Jan. 7, 2019

(87) PCT Pub. No.: WO2018/008994
PCT Pub. Date: Jan. 11, 2018

(65) Prior Publication Data
US 2019/0257024 A1    Aug. 22, 2019

(30) Foreign Application Priority Data
Jul. 7, 2016    (KR) .................. 10-2016-0086425

(51) Int. Cl.
*D06F 58/20* (2006.01)
*D06F 58/30* (2020.01)
(Continued)

(52) U.S. Cl.
CPC .............. *D06F 58/203* (2013.01); *A61L 2/04* (2013.01); *A61L 2/07* (2013.01); *A61L 2/26* (2013.01);
(Continued)

(58) Field of Classification Search
CPC ........ D06F 58/203; D06F 58/30; D06F 58/20; D06F 58/26; D06F 58/10; D06F 58/12;
(Continued)

(56) References Cited

U.S. PATENT DOCUMENTS 2,445,403 A * 7/1948 Mayerman .............. D06F 58/14
34/622
2,463,218 A * 3/1949 Travis ..................... D06F 58/14
34/60
(Continued)

FOREIGN PATENT DOCUMENTS

CN    101387073    3/2009
CN    101492875    7/2009
(Continued)

OTHER PUBLICATIONS

PCT International Search Report and Written Opinion in International Appln. No. PCT/KR2017/007214, dated Oct. 25, 2017, 9 pages (English translation).
(Continued)

*Primary Examiner* — Ismael Izaguirre
(74) *Attorney, Agent, or Firm* — Fish & Richardson P.C.

(57) ABSTRACT

The present invention relates to a clothes-handing apparatus comprising: a cabinet having a holder opening provided at an upper panel; an air moving part provided inside the cabinet so as to generate an air flow; a holder which is withdrawable from the cabinet through the holder opening and on which clothes are hung; and holder air holes provided at the holder so as to supply air to the clothes hung on the holder.

20 Claims, 16 Drawing Sheets

(51) Int. Cl.

| | |
|---|---|
| *D06F 58/26* | (2006.01) |
| *D06F 87/00* | (2006.01) |
| *A61L 2/04* | (2006.01) |
| *A61L 2/07* | (2006.01) |
| *A61L 2/26* | (2006.01) |
| *A61L 9/03* | (2006.01) |
| *A61L 9/16* | (2006.01) |
| *F24F 11/00* | (2018.01) |
| *F25B 21/02* | (2006.01) |
| *H01L 35/28* | (2006.01) |

(52) U.S. Cl.
CPC ............... *A61L 9/03* (2013.01); *A61L 9/16* (2013.01); *D06F 58/20* (2013.01); *D06F 58/26* (2013.01); *D06F 58/30* (2020.02); *D06F 87/00* (2013.01); *F24F 11/00* (2013.01); *F25B 21/02* (2013.01); *H01L 35/28* (2013.01); *A61L 2202/11* (2013.01); *A61L 2202/122* (2013.01); *A61L 2202/17* (2013.01); *A61L 2202/26* (2013.01); *F25B 2321/023* (2013.01); *F25B 2321/0251* (2013.01)

(58) Field of Classification Search
CPC .......... D06F 58/14; D06F 58/16; D06F 59/00; D06F 59/02; D06F 67/005; D06F 71/40; D06F 73/00; D06F 73/02; D06F 87/00; A61L 2/04; A61L 2/07; A61L 2/26; A61L 2202/11; A61L 2202/122; A61L 2202/17; A61L 2202/26; A61L 9/03; A61L 9/16; F24F 11/00; F25B 21/02; F25B 2321/023; F25B 2321/0251; A47B 61/00; A47B 61/02
See application file for complete search history.

(56) References Cited

U.S. PATENT DOCUMENTS

| | | | | |
|---|---|---|---|---|
| 3,576,079 A | * | 4/1971 | Hauser | ............... D06F 73/02 34/542 |
| 5,592,750 A | * | 1/1997 | Eichten | ................... D06F 59/02 223/70 |
| 5,687,278 A | * | 11/1997 | Turner | .................... D06F 73/00 219/211 |
| 6,327,792 B1 | * | 12/2001 | Hebert | ................. A43D 3/1491 34/104 |
| 7,032,336 B2 | * | 4/2006 | Bedretdinov | .......... A47G 25/72 38/14 |
| D616,621 S | * | 5/2010 | Prokop | ................... D06F 58/14 D32/58 |
| 2006/0054576 A1 | * | 3/2006 | Durham | ................. F26B 25/06 211/85.7 |
| 2014/0105783 A1 | * | 4/2014 | Levsen | ................... A61L 2/202 422/5 |
| 2015/0308699 A1 | * | 10/2015 | Dreossi | ................ D06F 39/006 122/15.1 |

FOREIGN PATENT DOCUMENTS

| | | | |
|---|---|---|---|
| CN | 202989619 | | 6/2013 |
| DE | 1039015 | A2 * | 9/2000 |
| EP | 1854916 | | 11/2007 |
| KR | 200438161 | | 1/2008 |
| KR | 1020080078367 | | 8/2008 |
| KR | 1020110079389 | | 7/2011 |
| KR | 101313591 | | 10/2013 |
| KR | 1020150015754 | | 2/2015 |
| KR | 1020160048355 | | 5/2016 |
| WO | WO2009020313 | | 2/2009 |

OTHER PUBLICATIONS

Extended European Search Report in European Application No. 17824550.2, dated Jan. 7, 2020, 7 pages.
Chinese Office Action in Chinese Application No. 201780041819.4, dated Jun. 18, 2020, 16 pages (with English translation).
CN Notice of Allowance in Chinese Appln. No. 201780041819.4, dated Mar. 19, 2021, 12 pages (with English translation).

* cited by examiner

[Fig. 1]
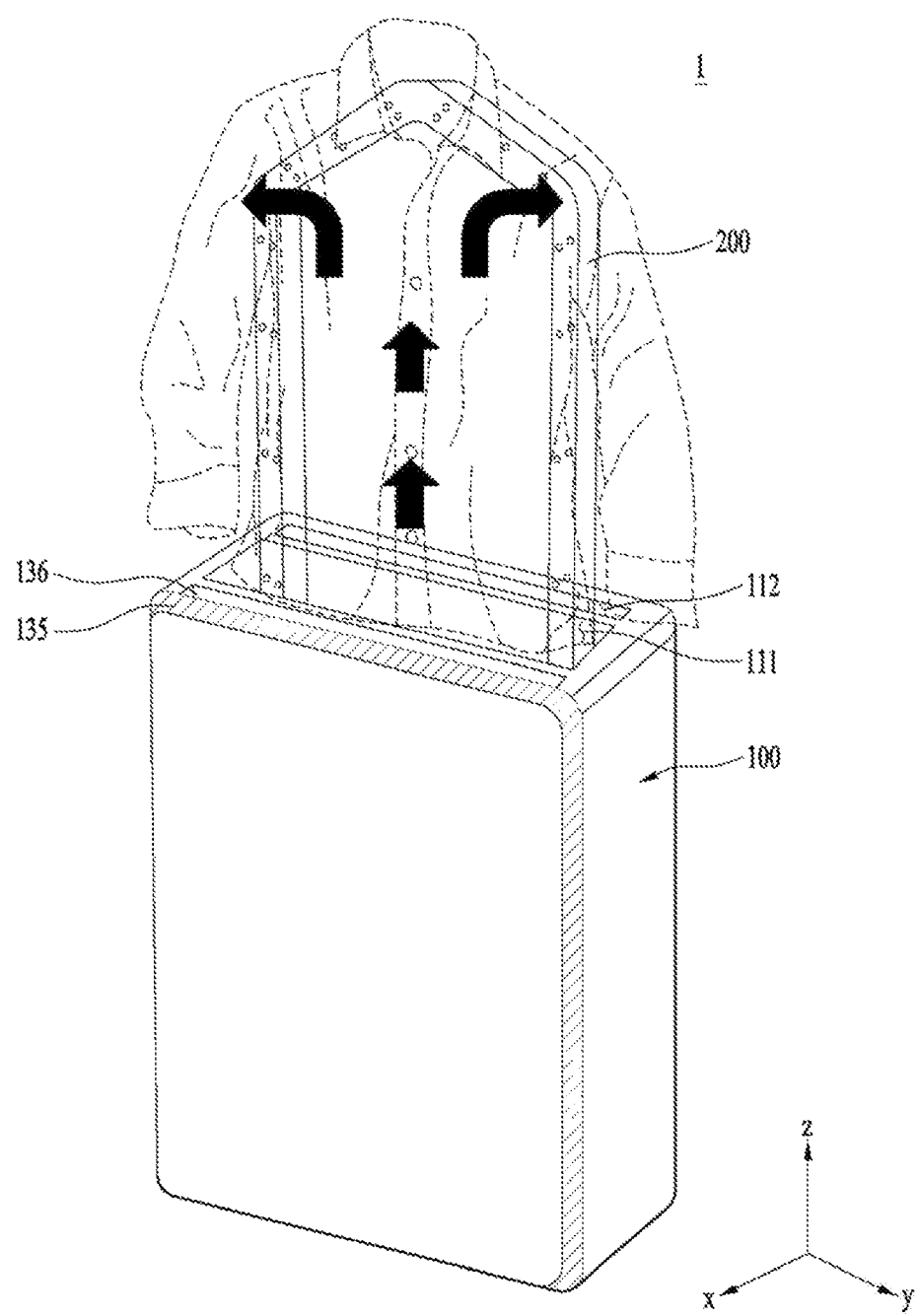

[Fig. 2]
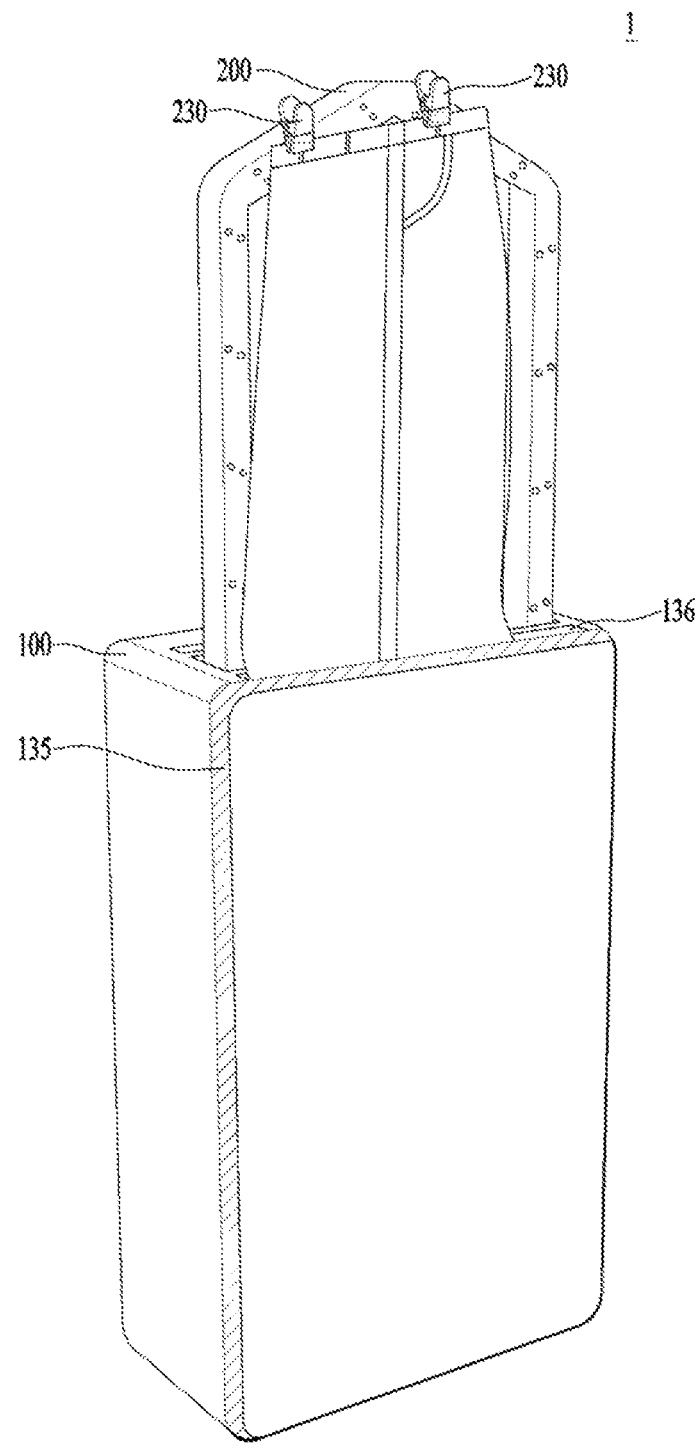

[Fig. 3]
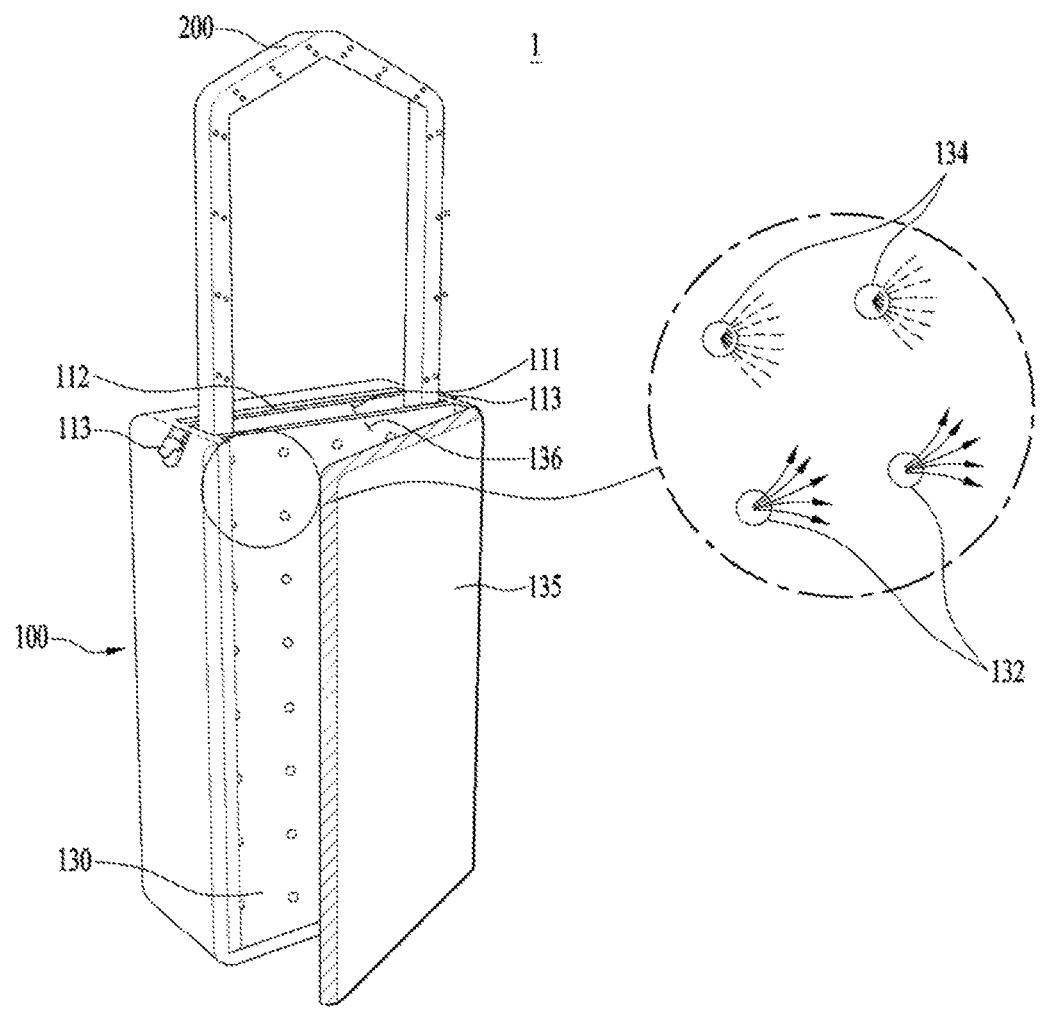

[Fig. 4]
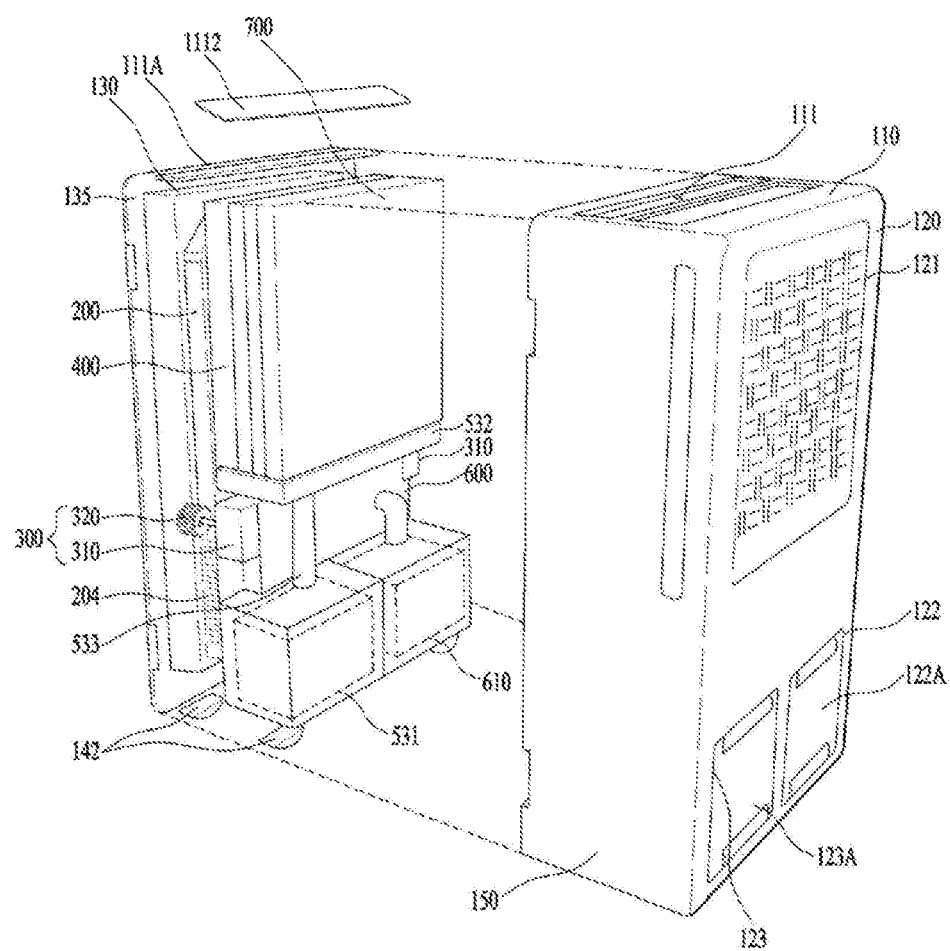

【Fig. 5】
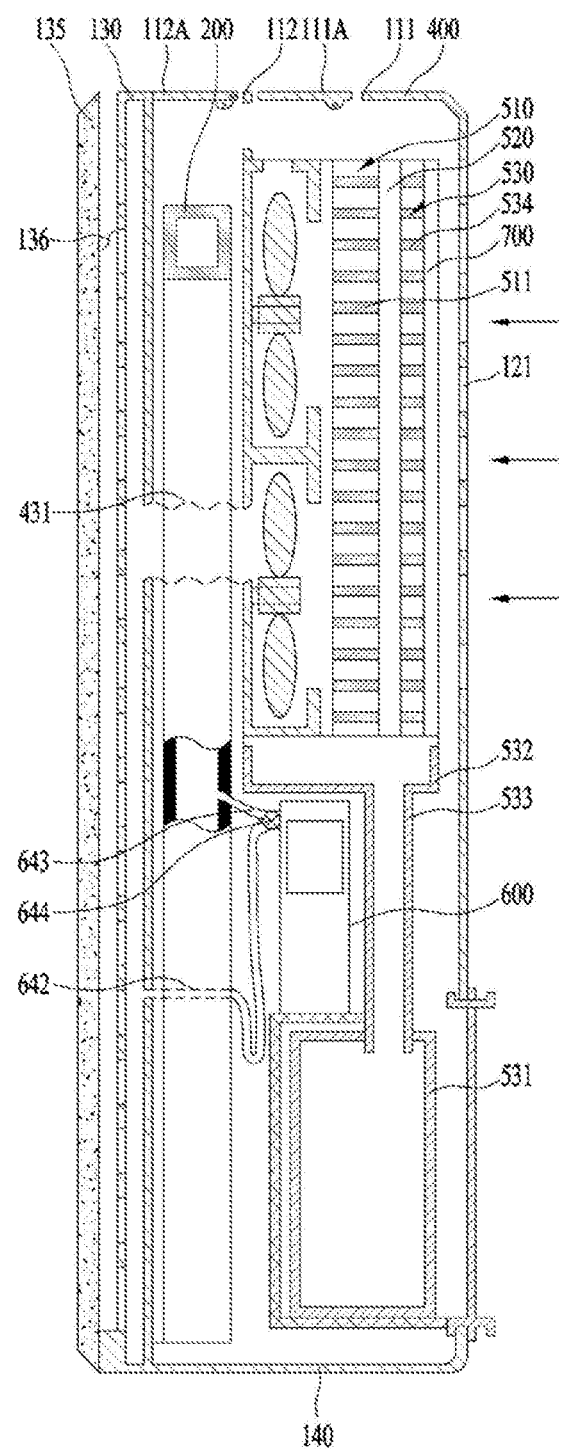

[Fig. 6]
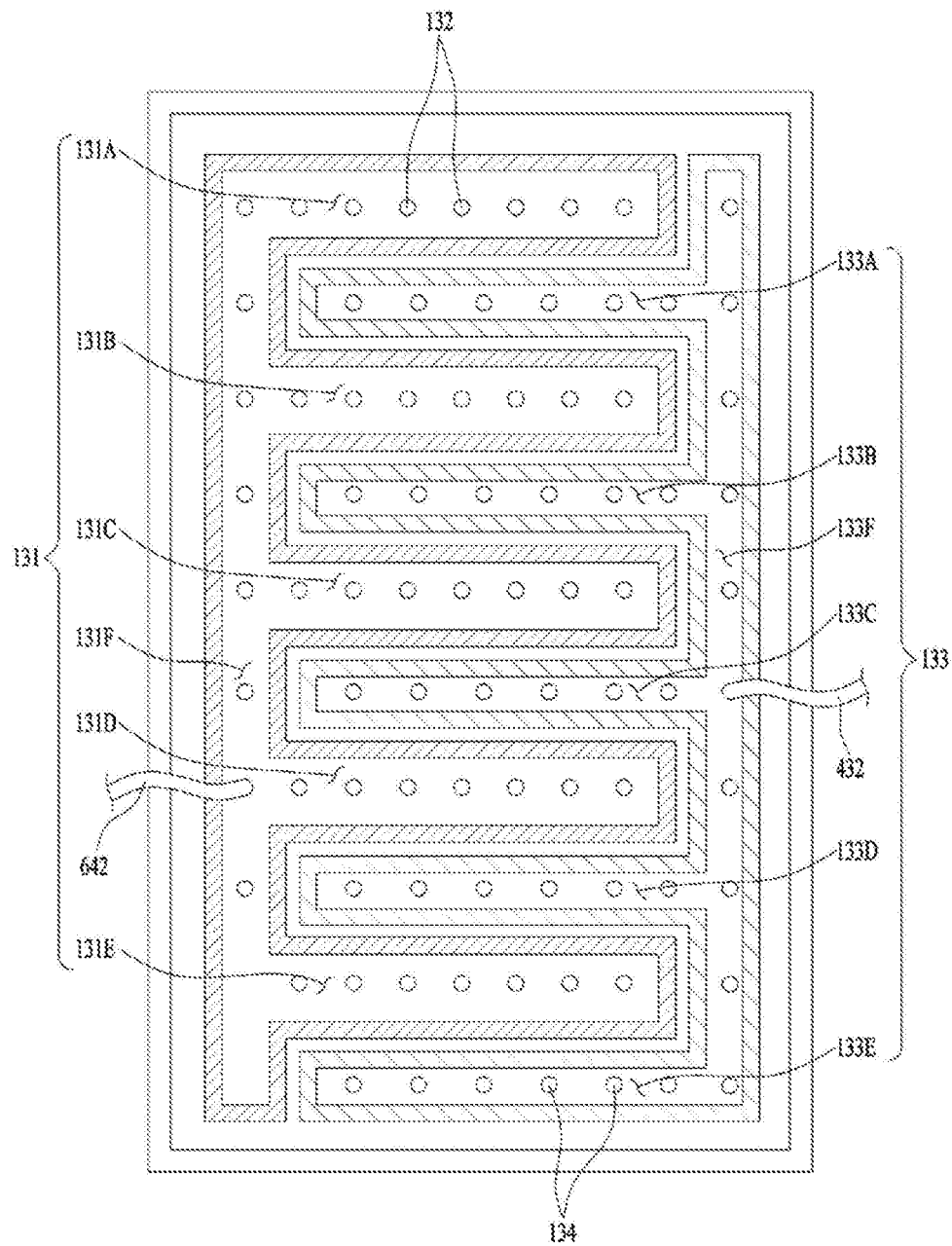

[Fig. 7]
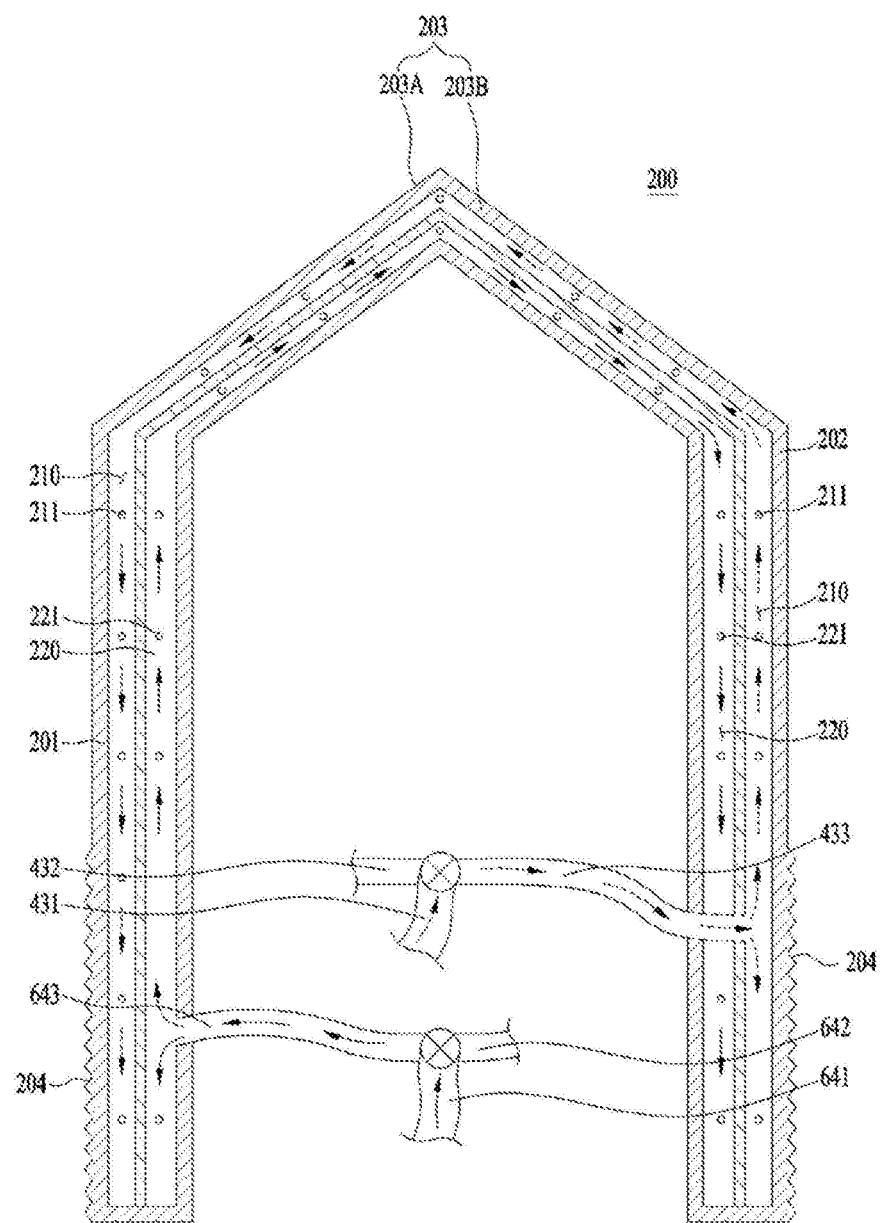

[Fig. 8]
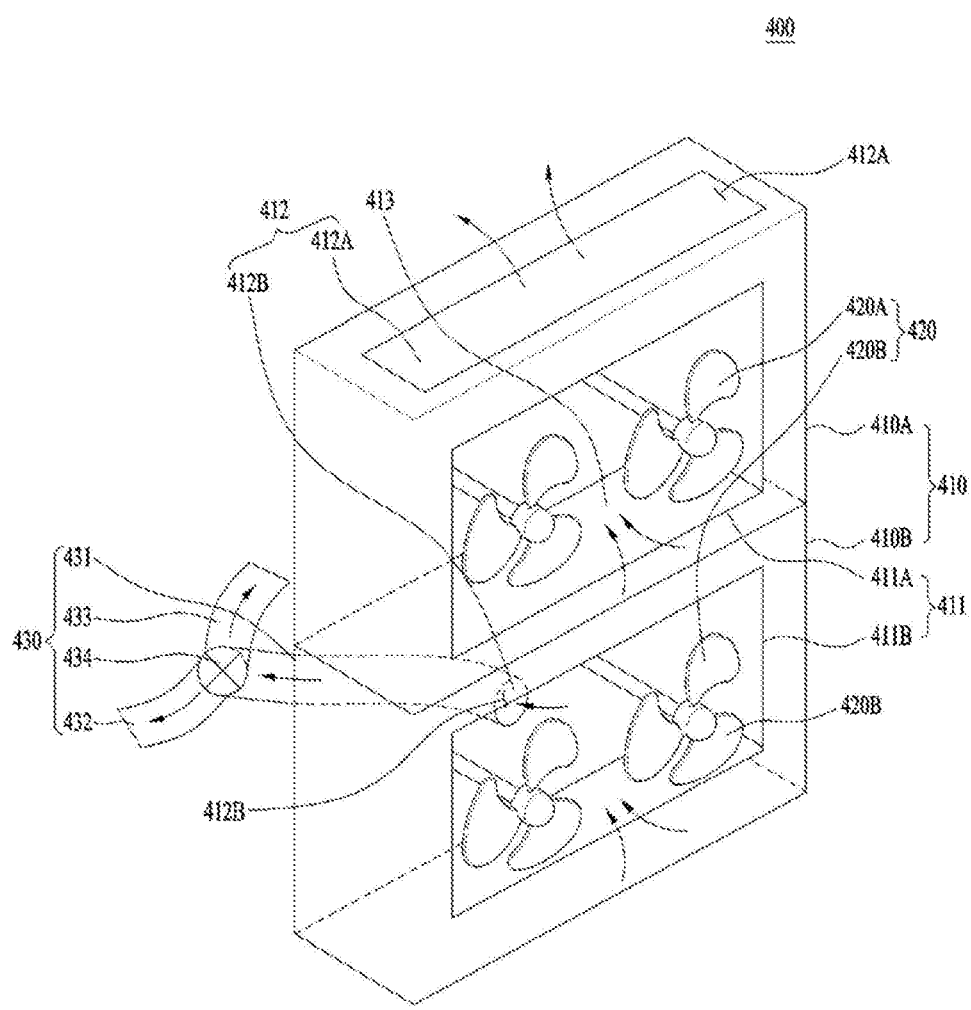

[Fig. 9]
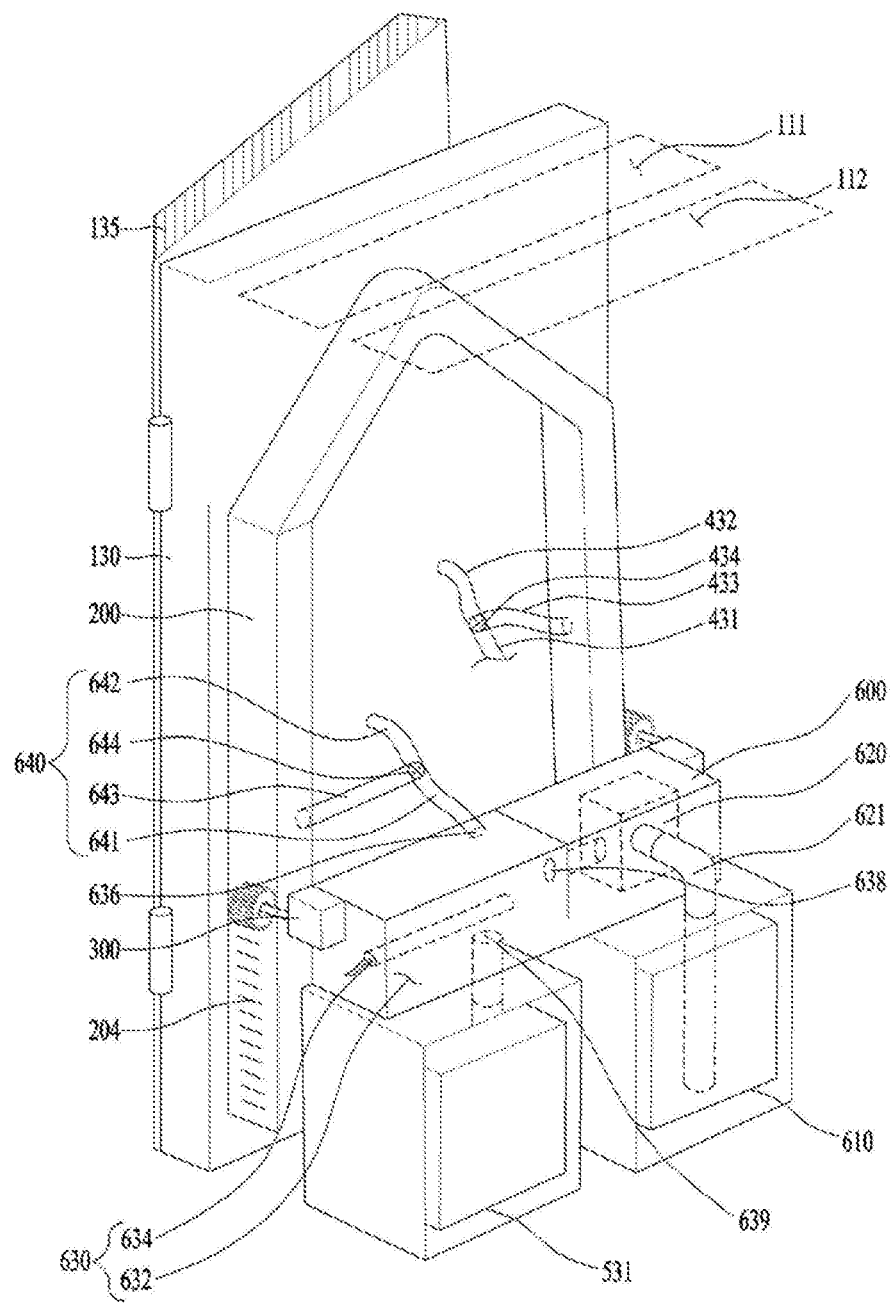

【Fig. 10a】
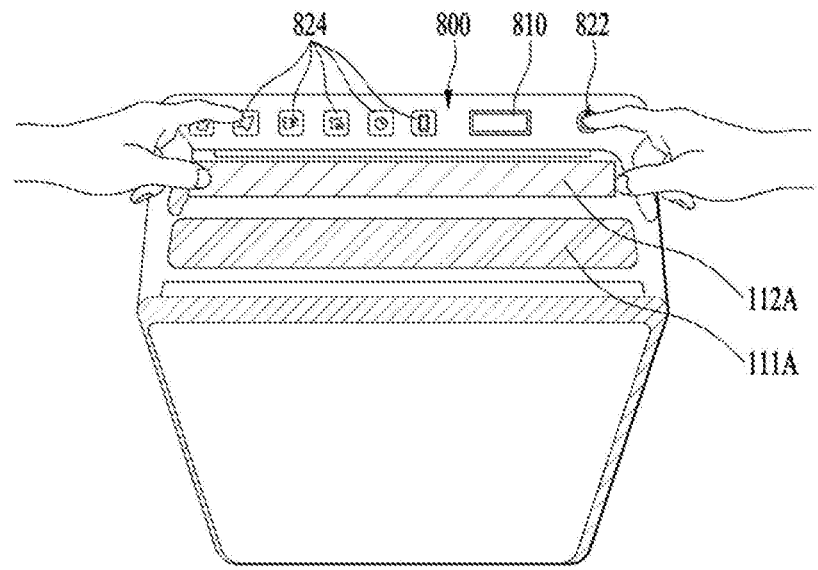
【Fig. 10b】
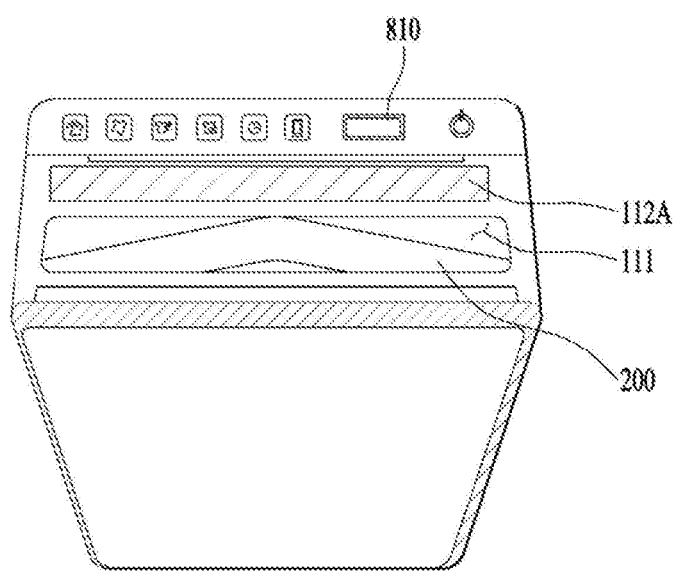

[Fig. 10c]
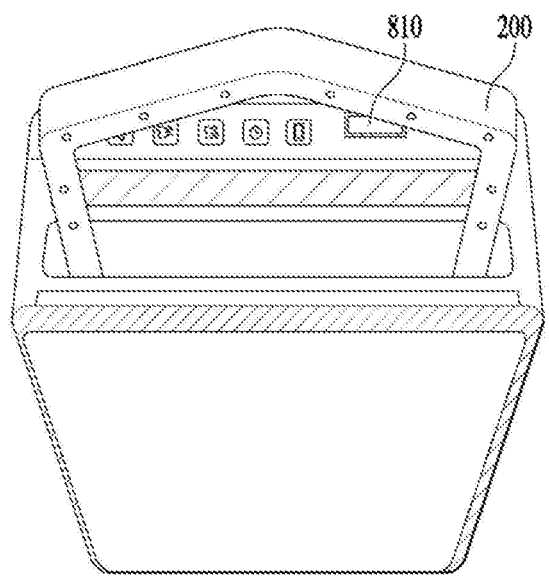
[Fig. 10d]
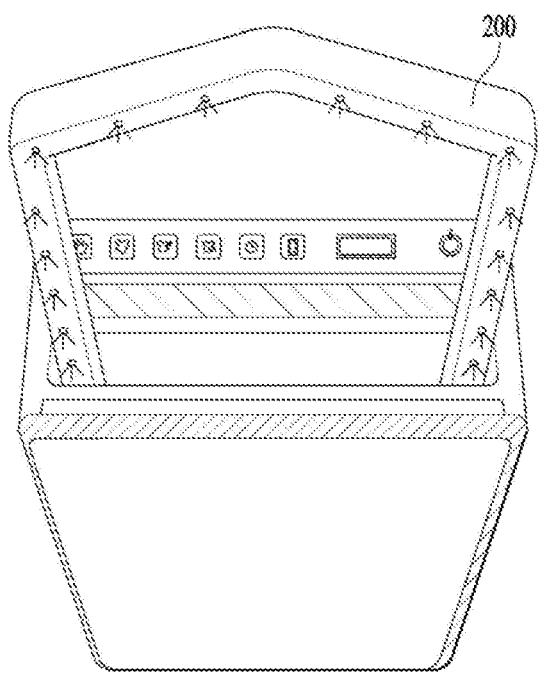

[Fig. 11a]
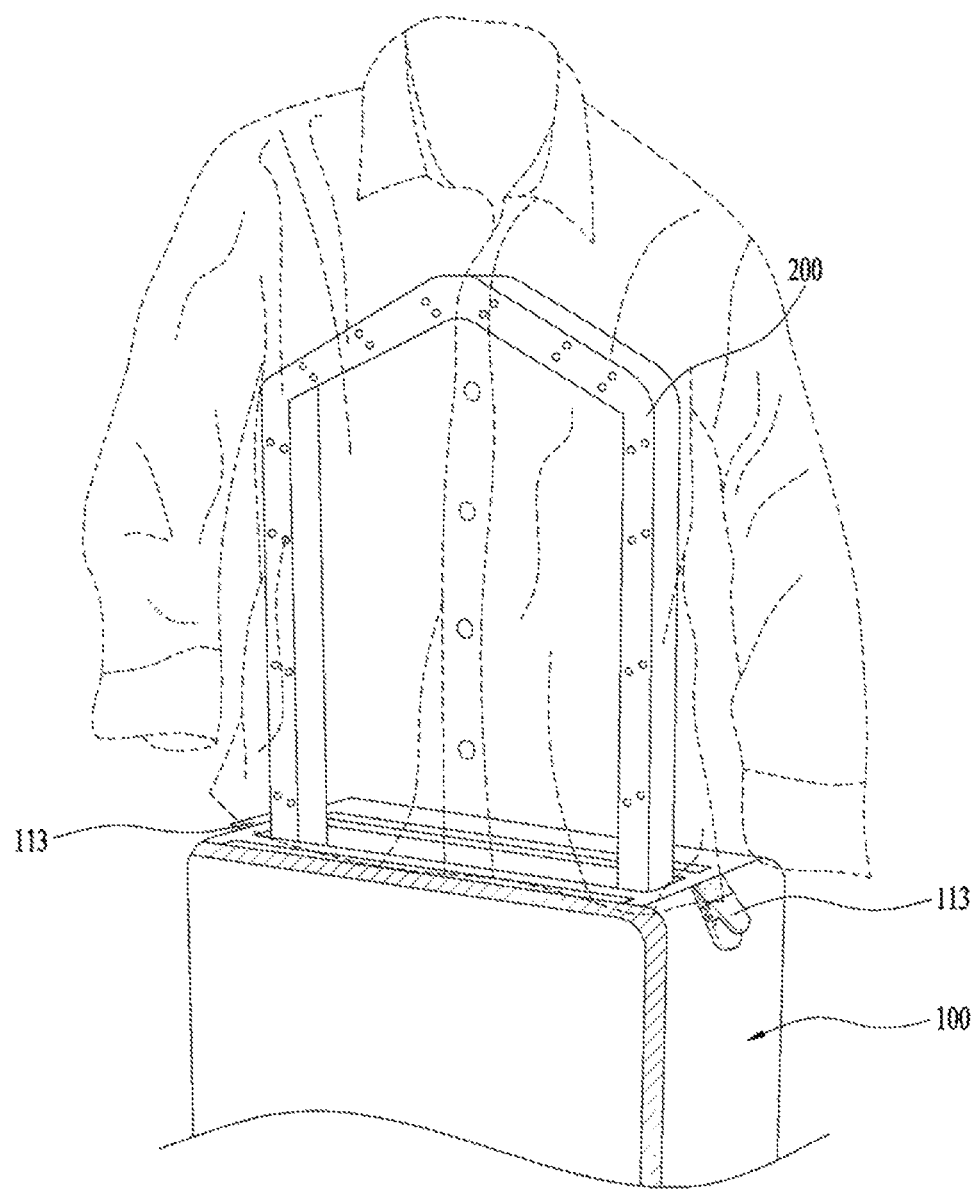

{Fig. 11b}
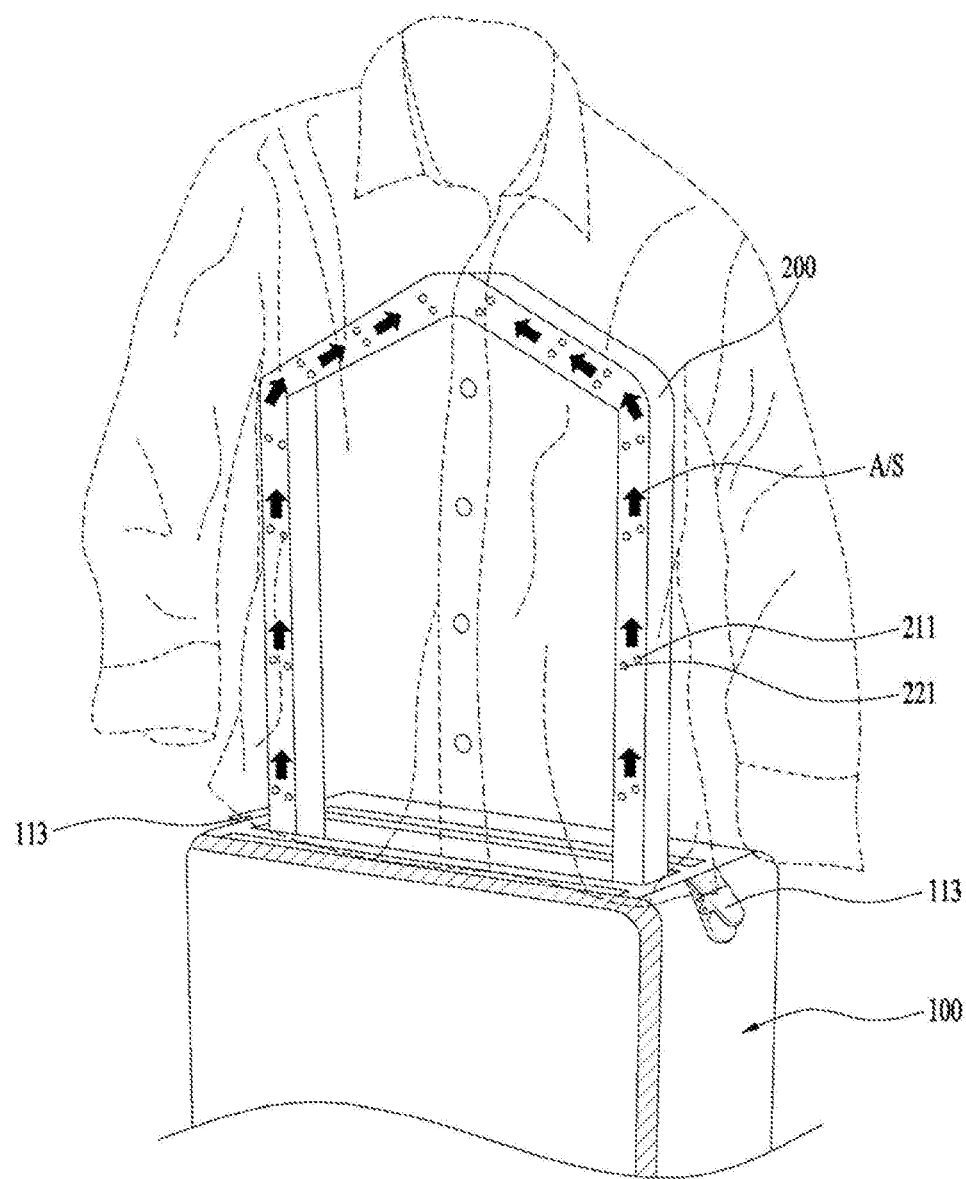

[Fig. 11c]
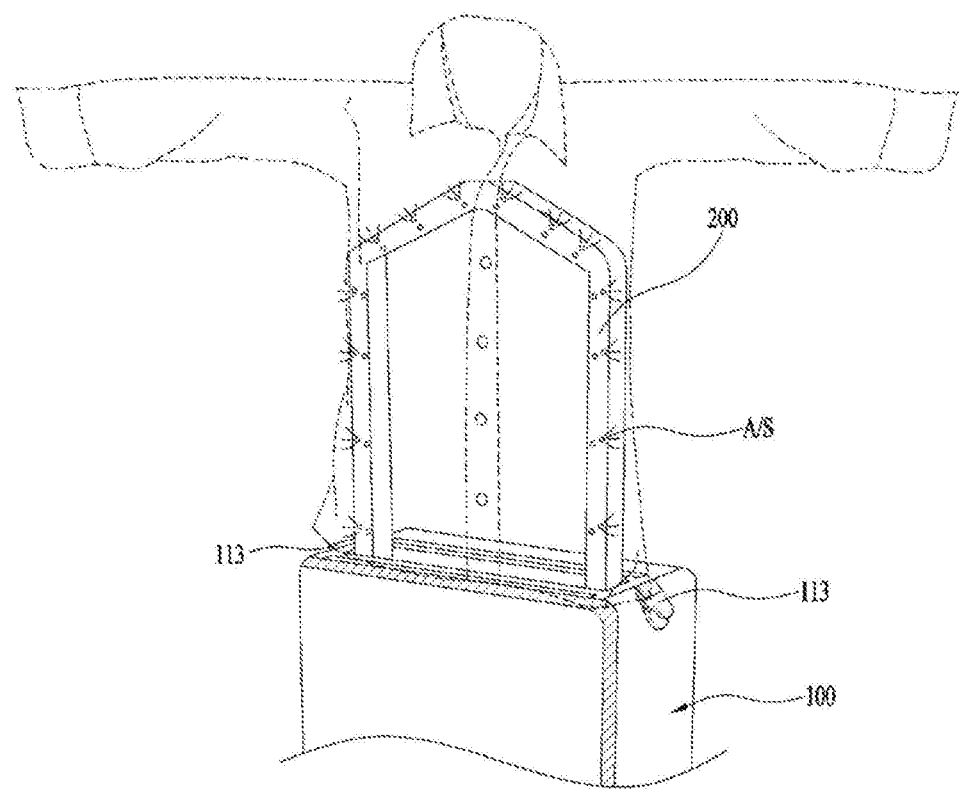

[Fig. 12a]
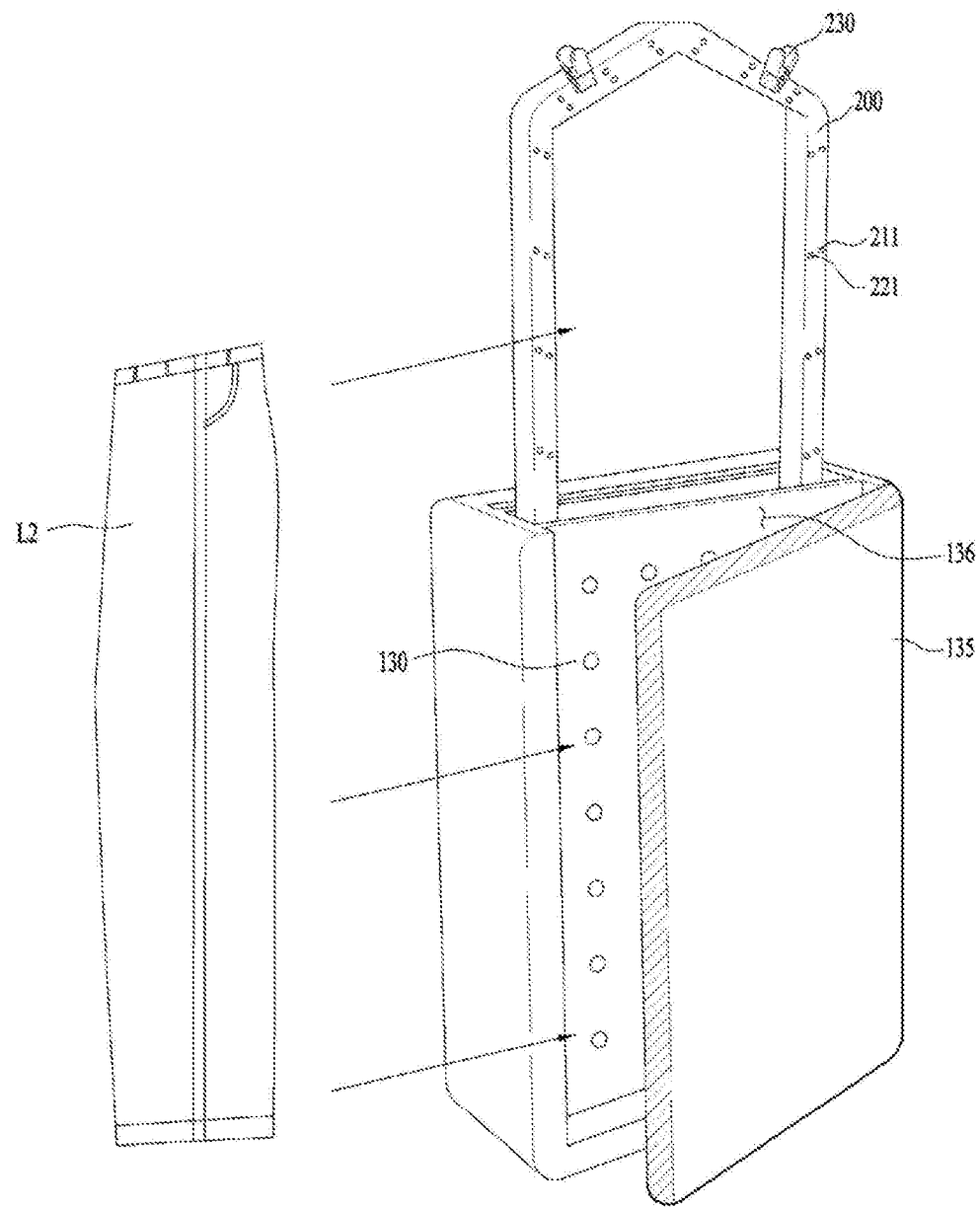

[Fig. 12b]
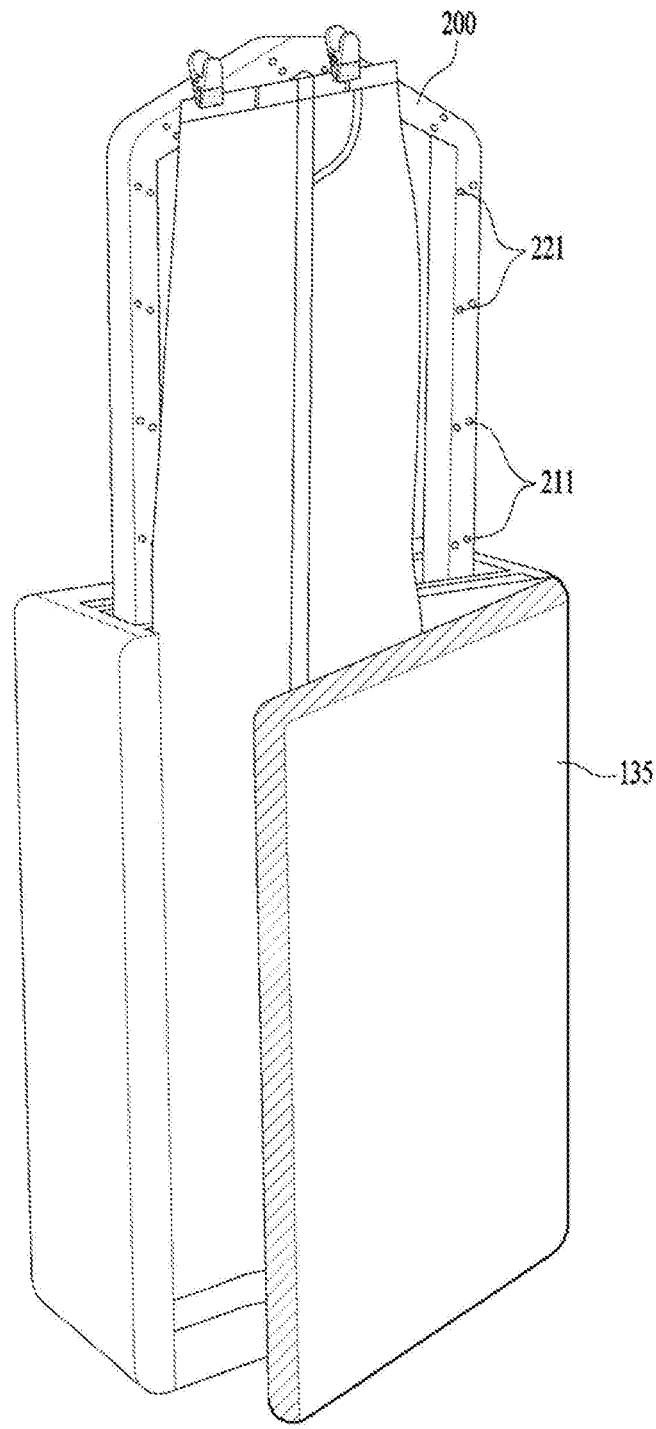

CLOTHES-HANDLING APPARATUS

CROSS-REFERENCE TO RELATED APPLICATIONS

This application is a National Stage application under 35 U.S.C. § 371 of International Application No. PCT/KR2017/007214, filed on Jul. 6, 2017, which claims the benefit of Korean Application No. 10-2016-0086425, filed on Jul. 7, 2016. The disclosures of the prior applications are incorporated by reference in their entirety.

FIELD

The present invention relates to a clothes-handling apparatus.

BACKGROUND

A conventional clothes-treating apparatus is a home electric appliance configured to perform one or more of washing, drying, refreshing and deodorizing processes for clothes. Among conventional clothes-treating apparatuses there is a washing or drying type that includes a cabinet, a tub provided in the cabinet to hold wash water and a drum provided in the tub to hold clothes so as to wash or dry the clothes.

Meanwhile, among such conventional clothes-treating apparatuses there is a refreshing or deodorizing type that includes a cabinet having a storage compartment, a door provided to open and close the storage compartment and a stand provided in the storage compartment to hang clothes so as to refresh or deodorize the clothes.

However, the above-noted clothes-treating apparatuses have a large volume and a heavy weight such that it is difficult to move them.

Moreover, the clothes that are worn just one or two times may not require chemical washing using a washing detergent or mechanical washing using the rotation of the drum (in other words, a washing method using a friction force between the drum and the clothes). Too often chemical or mechanical washing might cause damage to the clothes.

As single-person households are growing fast, the laundry that has to be washed becomes reduced and then there is a problem that such the chemical or mechanical washing may not be performed often.

Moreover, as the amount of fine dust is increasing, people desires to actuate a preliminary or simple washing process and sterilize or deodorize the clothes they worn after outdoor activities more and more.

DETAILED DESCRIPTION OF THE INVENTION

Technical Problem

To overcome the disadvantages, an object of the present invention is to address the above-noted and other problems and to provide a clothes-treating apparatus which is easy to move, with a small volume and a light weight.

Another object of the present invention is to provide a clothes-treating apparatus which may sterilize microbes and supply air or hot air to the clothes.

A further object of the present invention is to provide a clothes-treating apparatus which may adjust the humidity of the place where clothes are kept.

A still further object of the present invention is to provide a clothes-treating apparatus which may simply remove the wrinkles generated in the clothes worn by a user.

Technical Solution

To achieve these objects and other advantages and in accordance with the purpose of the embodiments, as embodied and broadly described herein, a clothes-treating apparatus comprises a cabinet comprising a holder opening provided in an upper panel; an air flow unit provided in the cabinet and configured to generate air flow; a holder retractable from the cabinet via the holder opening and configured to hang clothes thereon; and a holder air hole provided in the holder and configured to supply air to the clothes hung on the holder.

The clothes-treating apparatus may further comprise a heating unit provided in the cabinet to heat the air flowing towards the holder air hole; and a Peltier module provided in the cabinet to supply hot air via the holder air hole.

The clothes-treating apparatus may further comprise a steam generator provided in the cabinet and configured to generate steam; and a holder steam hole provided in the holder and configured to supply steam to the clothes hung on the holder.

The clothes-treating apparatus may further comprise an exhaustion hole provided in an upper surface of the cabinet, wherein air flow or hot air is supplied to the clothes hung on the holder via the exhaustion hole.

The clothes-treating apparatus may further comprise an iron panel rotatably provided in the front panel of the cabinet and the clothes hung on the holder may be located between the iron panel and the front panel.

The clothes-treating apparatus may further comprise a cabinet steam hole provided in the front panel and configured to spray steam there through.

The clothes-treating apparatus may further comprise a cabinet exhaustion hole provided in the front panel and configured to supply air flow or hot air.

The clothes-treating apparatus may further comprise at least one of a holder air path provided in the holder to provide an air path and a holder steam path provided in the holder to provide a steam path.

The clothes-treating apparatus may further comprise at least one of a front panel air path provided in the front panel to provide an air path and a front panel steam path provided in the front panel to provide a steam path.

In another aspect of the present invention, a clothes-treating apparatus comprises a cabinet comprising a holder opening provided in an upper panel; an air flow unit provided in the cabinet and configured to generate air flow; a holder retractable from the cabinet via the holder opening and configured to hang clothes thereon; and a holder air hole provided in the holder and configured to supply air to the clothes hung on the holder.

The clothes-treating apparatus may further comprise a Peltier module provided in the cabinet; and a heating unit provided in the cabinet, fixed to the Peltier module, and configured to heat the air flowing towards the holder air hole.

The clothes-treating apparatus may further comprise a steam generator provided in the cabinet and configured to generate steam; and a holder steam hole provided in the holder and configured to supply steam to the clothes hung on the holder.

The clothes-treating apparatus may further comprise an exhaustion hole provided in an upper surface of the cabinet and configured to supply heated air or not-heated air to the clothes hung on the holder.

The clothes-treating apparatus may further comprise an iron panel rotatably provided in the front panel of the cabinet and configured to press the clothes towards the front panel.

The clothes-treating apparatus may further comprise a cabinet steam hole provided in the front panel and configured to spray steam there through.

The clothes-treating apparatus may further comprise a cabinet exhaustion hole provided in the front panel and configured to exhaust heated air or not-heated air there through.

The clothes-treating apparatus may further comprise at least one of a holder air path provided in the holder to provide an air path and a holder steam path provided in the holder to provide a steam path.

The clothes-treating apparatus may further comprise at least one of a front panel air path provided in the front panel to provide an air path and a front panel steam path provided in the front panel to provide a steam path.

Advantageous Effects

Accordingly, the embodiments have following advantageous effects. According to at least one embodiment of the present disclosure, the clothes-treating apparatus may be easy to move, with a small volume and a light weight.

Furthermore, the clothes-treating apparatus may remove bad smell or humidity from the clothes worn by a user and sterilize microbes such as dust mites. Also, the clothes-treating apparatus may supply air or hot air to the clothes.

Still further, the clothes-treating apparatus may adjust the humidity of the place where clothes are kept.

Still further, the clothes-treating apparatus may simply remove the wrinkles generated in the clothes worn by the user.

BRIEF DESCRIPTION OF THE DRAWINGS

FIG. 1 is a diagram illustrating one embodiment of a clothes-treating apparatus in accordance with the prevent invention;

FIG. 2 is a diagram illustrating another embodiment of the clothes-treating apparatus;

FIG. 3 is a perspective diagram of the clothes-treating apparatus;

FIG. 4 is an exploded perspective diagram of the clothes-treating apparatus;

FIG. 5 is a sectional diagram of the clothes-treating apparatus;

FIG. 6 is a sectional diagram of a front panel provided in the clothes-treating apparatus;

FIG. 7 is a diagram illustrating a stand provided in the clothes-treating apparatus;

FIG. 8 is a diagram illustrating an air flow unit provided in the clothes-treating apparatus;

FIG. 9 is a diagram illustrating an inside of the clothes-treating apparatus;

FIG. 10 is a diagram illustrating one example of an initial operation performed in the clothes-treating apparatus;

FIG. 11 is a diagram illustrating one example of an operation when a top is hung; and FIG. 12 is a diagram illustrating one example of an operation when a bottom is hung.

DESCRIPTION OF SPECIFIC EMBODIMENTS

Referring to the accompanying drawings, exemplary embodiments of the present disclosure will be described in detail. Regardless of numeral references, the same or equivalent components may be provided with the same reference numbers and description thereof will not be repeated. For the sake of brief description with reference to the drawings, the sizes and profiles of the elements illustrated in the accompanying drawings may be exaggerated or reduced and it should be understood that the embodiments presented herein are not limited by the accompanying drawings.

Referring to an orthogonal coordinates system shown in FIG. 1, X-direction is defined as forward and Y-direction is defined as rightward and Z-direction is defined as upward. The definitions of such directions become criteria describing the present invention as follows.

FIG. 1 is a diagram illustrating one embodiment of a clothes-treating apparatus in accordance with the prevent invention. FIG. 2 is a diagram illustrating another embodiment of the clothes-treating apparatus. Referring to FIGS. 1 and 2, the clothes-treating apparatus in accordance with the present invention will be described.

Tops may be hung on the clothes-treating apparatus as shown in FIG. 1 or bottoms may be hung on the clothes-treating apparatus in accordance with the present invention as shown in FIG. 2. One or more of the air, hot air and steam may be supplied to the hung top or bottom and the hung top or bottom may be then deodorized, sterilized or wrinkle-free. Also, the clothes (the top or bottom) may be refreshed. Accordingly, a user is able to gain effects of clothes deodorization, drying, sterilization and wrinkle-removal before wearing the washed clothes or after wearing the clothes.

FIG. 3 is a perspective diagram of the clothes-treating apparatus. FIG. 4 is an exploded perspective diagram of the clothes-treating apparatus. FIG. 5 is a sectional diagram of the clothes-treating apparatus.

Hereinafter, referring to FIGS. 3 through 5, the structure of the clothes-treating apparatus will be described in detail.

Referring to FIGS. 3 and 4, the clothes-treating apparatus may include a cabinet 100; and a stand 200 that is retractable from the cabinet 100 and providing a predetermined space in which clothes are hung.

The cabinet 100 may include an upper panel 110 defining an upper surface; a rear panel 120 defining a rear surface; a front panel 130 defining a front panel 130 defining a front surface; a lateral panel 150 defining right and left surfaces; and a lower panel 140 defining a lower surface. Each of the panels may be fabricated as a separate piece and the panels are coupled to each other to form one cabinet 100.

The clothes-treating apparatus in accordance with the present invention may further include a wheel 142 provided in the lower panel 140 to allow the user to move the clothes-treating apparatus easily.

Meanwhile, a holder introduction opening 111 may be further provided in the upper panel 110. The holder 200 may be movable outside the cabinet 100 through the holder introduction opening 111.

The holder introduction opening 111 may be open and closed by an introduction opening cover 111A rotatably coupled to one side of the upper panel 110.

Meanwhile, the clothes-treating apparatus may further include an exhaustion hole 112 provided in the upper panel 110 to exhaust internal air of the cabinet 100 outside. The exhaustion hole 112 may be open and closed by an exhaustion cover 112A rotatably coupled to one side of the upper panel 110.

To fix the clothes to the cabinet 100, a first clothes-fixing unit 113 may be provided in the upper panel 110. The first clothes-fixing unit 113 may be fixed to the clothes hung on the holder 200. Accordingly, the clothes may be prevented from separating from the holder 200 by the air exhausted via the holder 200 or the exhaustion hole 112. Specifically, the first clothes-fixing unit 113 may be provided to fix a lower end of the clothing item, or top and it may be provided as tweezers or cloth-pins.

A suction hole 121 may be provided in the rear panel 120 to suck external air into the cabinet 100.

It is preferred to provide the suction hole 121 in an upper area of the cabinet, not a lower area, because foreign substances such as dusts is likely to be contained in the air located in the lower area of the cabinet 100.

Moreover, the clothes-treating apparatus may further include a water inlet tank 610 and a water outlet tank 531 that are located in the cabinet 100; a water inlet hole 122 provided in the rear panel 120 of the cabinet to facilitate the water inlet tank 610 insertable in the cabinet 100; and a water outlet hole 123 provided in the rear panel 120 of the cabinet to facilitate the water outlet tank 151 insertable in the cabinet.

The water inlet hole 122 may be open and closed by a water inlet hole cover 122A and the water outlet hole 123 may be open and closed by an outlet hole cover 123A.

A cabinet steam hole 132 may be provided in the front panel 130 to spray steam. A plurality of steam holes 132 may be provided in the front panel 130, spaced apart from each other.

Moreover, a cabinet exhaustion hole 134 may be provided in the front panel 130 to exhaust air. A plurality of cabinet exhaustion holes 134 may be provided in the front panel 130, spaced apart from each other.

The cabinet steam holes 132 and the cabinet exhaustion holes 134 may be alternately located in the front panel 130, spaced a preset distance apart from each other.

FIG. 6 is a sectional diagram illustrating the front panel in accordance with the present invention. Referring to FIG. 6, a steam path and an air path that are provided in the front panel will be described.

Referring to FIG. 6, the front panel 130 may include at least one of a front panel steam path 131 configured for flow of steam and a front panel air path 133 for flow of not-heated-air or heated-air (hot air).

The front panel steam path 131 may be connected to a steam connection path 640 which will be described later. The front panel steam path 131 may be configured to be supplied steam and temporarily store the steam therein before spraying the steam via the steam holes 132. The front panel steam path 131 may be in communication with the plurality of the cabinet steam holes 132. Accordingly, the steam drawn into the front panel steam path 131 may be sprayed outside the cabinet 100 via the plurality of the cabinet steam holes 132.

Meanwhile, the front panel air path 133 may be connected to an air connection path 430 which will be described later. The front panel air path 133 may be configured to be supplied the hot-heated air or hot air and temporarily store the supplied air therein via the cabinet exhaustion holes 134. The front panel air path 133 may be in communication with the plurality of the cabinet exhaustion holes 134.

When both the front panel steam path 131 and the front panel air path 133 are provided in the front panel 130, the shapes of the steam and air paths may affect the arrangement of the cabinet steam holes 132 and the cabinet exhaustion holes 134 that are provided in the front panel 130. To supply the steam, the air flow and the hot air to the clothes uniformly, it is important to arrange the cabinet steam holes 132 and the cabinet exhaustion holes 134 in the front panel 130 uniformly.

For that, the front panel steam path 131 may include a plurality of first, second, third, fourth and fifth steam paths 131A, 131B, 131C, 131D and 131E vertically spaced apart from each other; and a main steam path 131F connected with the plurality of the steam paths. The front panel air path 133 may include a plurality of first, second, third, fourth and fifth air paths 133A, 133B, 133C, 133D and 133E vertically spaced apart from each other; and a main air path 133F connected with the plurality of the air paths.

In this instance, the steam paths 131A, 131B, 131C, 131D, and 131E and the air paths 133A, 133B, 133C, 133D and 133E may be arranged vertically and alternately (in other words, alternately along the height direction of the cabinet). As one example, the first steam path 131A, the first air path 133A, the second steam path 131B, the second air path 133B and the like may be vertically arranged in order.

Meanwhile, referring to FIG. 3 again, the clothes-treating apparatus in accordance with the present invention may include an iron panel 135 rotatably coupled to one side of the cabinet 100. The iron panel 135 may be coupled to the front surface or the front panel 130 of the cabinet 100.

The iron panel 135 may maintain a state of being fixed to the front panel 130 by a locking mechanism (not shown). The locking mechanism may be a latch structure or a magnetic material.

When the iron panel 135 is secured to the front panel 130 by the locking mechanism, the clothing located between the iron panel 135 and the front panel 130 may be pressed by the iron panel 135 and the wrinkles remaining in the clothing may be removed by the iron panel.

In contrast, a clothes-accommodation space may be further provided between the iron panel 135 and the front panel 130 to prevent the clothes from becoming pressed by the iron panel. The clothes-accommodation space may be recessed in a direction that becomes farther from the direction of the iron panel 135. The wrinkles caused on the clothes located in the clothes-accommodation space may be removed by the weight of the clothes and the steam and air supplied from the front panel.

FIG. 7 is a diagram illustrating the holder provided in the clothes-treating apparatus in accordance with the present invention. Referring to FIG. 7, the holder will be described in detail.

The holder 200 may be movable within the cabinet 100. When trying to hang clothes on the holder 200, the user is able to draw the holder outside the cabinet 100 via a holder opening 111. The clothing (top or bottom) may be hung on the drawn holder 200. A top or jacket may be hung by covering the holder 200 and a bottom may be hung on the holder 200 by using the tweezers or cloth-pins.

The holder 200 may include a holder steam hole 211 provided in an outer surface to spray steam to the clothing; and a holder steam path 210 provided in communication with the holder steam hole 211 to supply steam to the holder steam hole 211.

The holder steam hole 211 may be provided in the outer surface of the holder 200 and include a plurality of holes with different heights. Accordingly, steam can be supplied to the entire area of the clothing uniformly. The holder steam path 210 may be provided in the holder 200.

The holder 200 may further include a holder air hole 221 provided in the outer surface of the holder to supply air to the clothing; and a holder air path 220 provided in communication with the holder air hole 221 to supply air to the holder air hole 221.

The holder air hole 221 may be provided in the outer surface of the holder 200 and include a plurality of holes with different heights. Accordingly, air may be supplied to the entire area of the clothing uniformly. The holder air path 220 may be provided within the holder 200. The holder air path 220 and the holder steam path 210 may be provided as independent paths that are not in communication with each other.

The holder 200 may include a first vertical member 201 vertically provided (or along a height direction of the cabinet); a second vertical member 202 provided along the height of the cabinet, spaced a preset distance apart from the first vertical member 201; and a connection member 203 provided to connect the first vertical member 210 to an upper end of the second vertical member 202.

The connection member 203 may include a first connection material 203A upwardly extended from one end of the first vertical member 201; and a second connection material 203B upwardly extended from one end of the second vertical member 202. The first connection material 203A and the second connection material 203B may be connected with each other.

Meanwhile, the clothes-treating apparatus in accordance with the present invention may include a first clothes-fixing unit (230, see FIG. 2) provided in the holder 200 to fixedly hang the clothing on the holder 200. The second clothes-fixing unit 230 may be provided in an upper area of the holder 200 and fix one end of the clothing (especially, bottom). As one example, the second clothes-fixing unit 230 may be provided as a pair of tweezers or cloth-pins.

The holder 200 may be retractable from the inside to the outside the cabinet 100 via the holder introduction opening. When trying to move the holder 200 outwardly, the only thing the user has to do is lifting an upper end of the holder 200 and the holder 200 is then able to be moved outwardly.

Meanwhile, as shown in FIG. 4, a drive unit 300 may be provided in accordance with the present invention and the drive unit 300 may be configured to move the holder 200. The drive unit 300 may include a motor 310 provided in the cabinet 100; and a drive gear 320 that is rotatable by a shaft provided in the motor 310.

The drive gear 320 may engage with a rack gear 204 provided in an outer surface of the holder 200 and become rotatable in clockwise and counter-clockwise directions to be movable upwards or downwards along the rotational directions of the drive gear 320. Accordingly, the holder 200 may be automatically movable upwards and downwards via the holder introduction opening 111.

FIG. 8 is a diagram illustrating an air flow unit provided in the clothes-treating apparatus. Referring to FIGS. 5 through 8, the air flow unit will be described.

The clothes-treating apparatus may include the air flow configured to generate air flow so as to exhaust air outside the cabinet. The air flow unit 400 may be provided in the cabinet and the air may be exhausted outside the cabinet via at least one of the exhaustion hole 112, the cabinet exhaustion hole 134 and the holder air hole 221.

The air flow unit 400 may include a fan 420 configured to generate air flow while rotating; and a fan housing 410 provided to define a predetermined space for installing the fan 420. A shaft of the fan may be perpendicular to a surface defined by the rear panel 120.

Once the air flow is generated by the rotation of the fan 420, external air may be drawn into the cabinet via the suction hole 121.

The fan housing 410 includes an air inlet hole 411 for drawing external air; and an air outlet hole 412 for exhausting internal air outside.

It is preferred that the air inlet hole 411 is provided to face the suction hole 121 of the rear panel 120. The air outlet hole 412 may include a first air outlet hole 412A in communication with the exhaustion hole 112 or the holder introduction opening 111; and a second air outlet hole 412B in communication with the cabinet exhaustion hole 134 or the holder air hole 221.

The first air outlet hole 412A is provided in a top surface of the hand housing 410 and the air flow generated by the rotation of the fan is exhausted via the exhaustion hole 112 or the holder introduction opening 11 provided over the first air outlet hole 412A via the first air outlet hole 412A.

The second air outlet hole 412B may be connected with the cabinet exhaustion hole 134 or the holder air hole 221 by the air connection path 430.

The air connection path may include a first air connection path 432 connected with the front panel air path 133; and a second air connection path 433 connected with the holder air path 220 provided in the holder 200.

The first air connection path 432 and the second air connection path 433 may be branched at the main air connection path 431 connected with the second air outlet hole 412B, respectively. In this instance, a three-way valve 434 may be provided among the main air connection path 431, the first air connection path 432, the second air connection path 433 to adjust the air drawn into the first air connection path 432 or the second air connection path 433. Accordingly, the amount of the air flow at the cabinet exhaustion hole 134 or the amount of the air flow spray in the holder air hole 221 may be adjusted. The main air connection path 431, the first air connection path 432 and the second air connection path 433 may be provided as extendable hoses, respectively.

To differently control the air flow drawn via the first air outlet hole 412A, the fan housing 410 may include a partition wall 413 provided to partition the internal space of the fan housing 410 off; first and second fan housings 410A and 410B that are partitioned off by the partition wall. The fan 420 may include a first fan 420A that is rotatable within the first fan housing 410A; and a second fan 420B that is rotatable in the second fan housing 410B.

In this instance, the air inlet hole 411 may include a first air inlet hole 411A provided in the first fan housing 410A; and a second air inlet hole 411B provided in the second fan hosing 410B. The first air outlet hole 412A may be provided in the first fan housing 410A and the second air outlet hole 412B may be provided in the second fan housing 410B.

The first air outlet hole 412A may be provided in the top surface of the first fan housing 410A and connected with a connection duct (not shown). The second air outlet hole 412B may be provided in a front surface of the second fan housing 410B. In other words, the second air outlet hole 412B may be provided in an area of the second fan housing 410B which faces the second air inlet hole 411B.

Accordingly, the clothes-treating apparatus may be configured to supply air to the exhaustion hole or the holder introduction opening 111 by driving the first fan 420A and air to the cabinet exhaustion hole 134 or the holder air hole 221 by driving the second fan.

As shown in FIG. 5, the clothes-treating apparatus in accordance with the present invention may include a heating unit 510 configured to generate hot air by heating the flowing air; and a Peltier module 520 provided behind the heating unit 510. The heating unit 510 may be provided in a rear surface of the fan housing 410.

The heating unit 510 and the Peltier module 520 may be in contact with each other. The heating unit 510 may include a plurality of plate-shaped heating pins having one ends that are in contact with the Peltier module 520, respectively.

The plurality of the plate-shaped heating pins 511 may be spaced a preset distance apart from each other to provide a predetermined space in which air can flow. It is preferred that the plurality of the plate-shaped heating pins 511 is made of metal having a high heat conductivity.

When an electric current flows to the Peltier module 520 in one direction, heat is generated in one surface of the Peltier module 520 and heat absorption is generated in the other surface. When an electric current flows in the reverse direction, the heat absorption is generated in one surface and the heat is generated in the other surface. The heating unit 510 is provided in the front surface of the Peltier module 520, in contact, and the direction of the electric current is selected to cause the heat generation of the front surface.

Moreover, the fan housing 410 is provided in front of the heating unit 510. More specifically, the other end of the plate-shaped pin 511 forming the heating unit 510 may be in contact with a rear surface (the area having the air inlet hole) of the fan housing 410.

The front surface heated by the electric current flowing to the Peltier module 520 heats the plate-shaped heating pins 511 and the air flowing through the spaces formed in each two of the plate-shaped heating pins 511 is heated by the heated plate-shaped heating pins 511 to be changed into hot air. Accordingly, the hot air may be supplied to the clothing via one or more of the exhaustion hole 112, the holder introduction opening 111, the cabinet exhaustion hole 134 and the holder air hole 221.

Meanwhile, the clothes-treating apparatus in accordance with the present invention may include a cooling unit 530 configured to remove humidity from the air. The cooling unit 530 may be provided in contact with the rear surface of the Peltier module 520. The cooling unit 530 may be configured of a plurality of plate-shaped cooling pins 534 having one ends in contact with the rear surface of the Peltier module 520, respectively. Air is heated in the front surface of the Peltier module 520 and air is cooled in the rear surface of the Peltier module. Accordingly, condensate is likely to be generated in the plate-shaped cooling pins 534.

The plurality of the plate-shaped cooling pins may be spaced a preset distance apart from each other and a predetermined space in which air can flow may be formed. In addition, it is preferred that each of the plate-shaped cooling pins 534 is made of metal having a high heat conductivity.

When try to generate hot air by using the Peltier module 520, the air drawn into the cabinet via the suction hole 121 by the rotation of the fan 420 may be cooled while passing between each two of the plate-shaped cooling pins 534. Accordingly, the moisture contained in the air is likely to be condensed on surfaces of the cooling pins 534. The air that becomes dry while passing through the cooling pins 534 may be heated while passing through the plate-shaped heating pins 511. After that, the heated air may be supplied to the clothing hung outside the cabinet via the air outlet holes 412A and 412B.

Meanwhile, the clothes-treating apparatus in accordance with the present invention may include a condensate trap 532 configured to temporarily collect the condensate condensed from the cooling pins 534; and a condensate drainage unit 533 configured to drain the water from the condensate trap 532. The condensate trap 532 is provided in a lower area of the cooling unit 530 and the condensate drainage unit 533 drains the condensate by connecting a lower surface of the condensate trap with the water outlet tank 531.

FIG. 9 is a diagram illustrating the inside of the clothes-treating apparatus. Referring to FIG. 9, a steam supply unit 600 provided in the clothes-treating apparatus will be described. The clothes-treating apparatus in accordance with the present invention may include the steam supply unit 600 configured to supply steam to clothes.

The steam supply unit 600 may be provided in the cabinet 100 and include a water inlet tank 610 provided to temporarily collect water; and a steam generator 630 configured to phase-change the water collected in the water inlet tank 610 into steam.

The water inlet tank 610 may be detachably provided in the cabinet 100 via a water inlet hole 122 provided in the rear panel 120.

The steam generator 630 may include a pump 620 configured to pump the water from the water inlet tank 610; a water storage 632 configured to temporarily store the pumped water; and a heater 634 provided in the water storage 632 and configured to heat and phase-change the water into steam. The water inlet tank 610, the pump 620 and the water storage 632 may be connected with each other by a water supply path 621.

The water storage 632 includes a water inlet hole 638 configured to be supplied water in communication with the water supply path 621; and a steam outlet hole 636 in communication with the water storage 632 to exhaust the steam generated in the water storage 632.

In case the pump 620 is provided, the water collected in the water inlet tank 610 may be supplied to the steam generator 630 by the pump. Accordingly, the steam generator 630 may be provided higher than the water inlet tank 610. The water discharged from the pump 620 may be moved to the water storage 632 via the water inlet hole 638 provided in the water storage 632.

The steam generated by the steam generator 630 may be sprayed or supplied to the clothing via the cabinet steam holes 132 provided in the front panel 130 or the holder steam holes 211 provided in the holder 200.

The steam outlet hole 636 may be connected with the cabinet steam hole 132 or the holder steam hole 211 by the steam connection path 640.

The steam connection path 640 may include a first steam connection path 642 connected with the front panel steam path 131; and a second steam connection path 643 connected with the holder steam path 210.

The first steam connection path 642 and the second steam connection path 643 may be branched from the main steam connection path 641 connected with the steam outlet hole 636.

In this instance, a 3-way valve 644 may be provided among the main steam connection path 641, the first steam connection path 642 and the second steam connection path 643 to adjust the amount of the steam drawn into the first steam connection path 642 or the second steam connection path 643 and then adjust the amount of the steam sprayed via the cabinet steam hole 132 or the holder steam hole 211.

The main steam connection path 641, the first steam connection path 642 and the second steam connection path 643 may be provided as extendible hoses, respectively.

Meanwhile, as shown in FIG. 5, the clothes-treating apparatus in accordance with the present invention may further include an ionizer 700 configured to emit an ion together with the heated air or not-heated air.

The ionizer 700 may be provided between the air flow unit 400 and the rear panel 120. Accordingly, the air flow generated by the air flow unit 400 may pass through the ionizer 700. More specifically, the ionizer 700 may be provided between the rear panel 120 and the cooling unit 530.

When the heated air or not-heated air is supplied to the clothing via at least one of the exhaustion hole 112, the holder introduction opening 111, the cabinet exhaustion hole 134 and the holder air hole 221, the ionizer 700 is actuated and a large amount of icons are sprayed to the clothing from the ionizer 700, together with air. Accordingly, the bacteria or germs may be destroyed by the spraying of the icons and air.

FIG. 10 is a diagram illustrating one example of an initial operation performed in the clothes-treating apparatus. FIG. 11 is a diagram illustrating one example of an operation when a top is hung on the holder 200. FIG. 12 is a diagram illustrating one example of an operation when a bottom is hung on the holder 200.

Hereinafter, referring to FIG. 10, the initial operation of the clothes-treating apparatus in accordance with the present invention will be described.

As shown in FIG. 10A, the clothes-treating apparatus may include a control panel 800 configured to control the clothes-treating apparatus; and a controller (not shown) connected with the control panel 800.

The control panel 800 may be provided in the upper panel 110 and it is preferred that the control panel 800 is provided behind the exhaustion hole 112.

The control panel 800 may include an input unit 822 and 824 configured to receive an input of a command from the user; and a display unit 810 configured to display the input command or a current state of the clothes-treating apparatus. The input unit 822 and 824 may include a power button unit 822; and a course selection button unit 824. The display unit 810 may display the input command or currently actuated course of the clothes-treating apparatus.

When the user pushes the power button unit 822, the electric power is supplied to the clothes-treating apparatus to actuate the display unit 810 and the course selection button unit 824. Accordingly, when the user pushes the course selection button unit 824, the current state becomes a state where a specific course is performed. In this instance, the user is able to push the course selection button unit 824 and the controller (not shown) controls the holder 200 to be retracted from the cabinet 100 via the holder opening 111 (see FIGS. 10B and 10C).

Moreover, the controller (not shown) performs the pushed specific course that is stored in the course selection button unit 824. The specific course is actuated to supply air flow or hot air and steam to the clothing hung on the holder (see FIG. 10D).

As shown in FIG. 11A, to dry, sterilize, refresh and perform wrinkle-removal for a no-dried top, a top with winkles and a top worn one or two times, the user is able to hang an open bottom of the top on the holder 200 like covering the holder 200 retracted from the cabinet 100. The user is able to fixedly put the top on the holder by fixing the open bottom of the top to the first clothes-fixing unit 113. In this instance, the hung clothing may be provided with at least one of the steam (S) and air (A) via the holder steam holes 211 of the holder air holes 221 which are provided in the holder 200 as shown in FIG. 11B. The hung clothing may be dried or refreshed by the air flow as shown in FIG. 11 such that it can be in a no-sticky state when it comes into contact with the user's skin.

As shown in FIGS. 12A and 12B, to dry, sterilize, refresh and perform wrinkle-removal for a no-dried bottom, a bottom with winkles and a bottom worn one or two times, the user is able to hang the bottom on the second clothes-fixing unit 230 provided in the upper end of the holder 200 retracted from the cabinet 100. After that, the user may fix the bottom between the front panel 130 and the iron panel 135 and remove the wrinkles from the bottom by pressing the bottom.

Moreover, at the same time when pressing the bottom by using the iron panel 135, at least one of the steams, air flow and hot air may be supplied to the clothing via the cabinet steam holes 132 and the cabinet exhaustion holes 134 which are provided in the front panel 130. Accordingly, the bottom may be dried, sterilized and refreshed and especially, wrinkles may be effectively removed.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A clothes-treating apparatus comprising:
a cabinet comprising:
an upper panel that defines a holder opening, and
a rear panel that defines one or more suction holes configured to receive air from an outside of the cabinet and positioned at an upper portion of the rear panel;
an air flow unit located in the cabinet and configured to generate air flow; and
a holder configured to insert into the cabinet through the holder opening and configured to hang clothes thereon, wherein the holder defines a holder air hole configured to supply air to the clothes hung on the holder.

2. The clothes-treating apparatus of claim 1, further comprising:
a Peltier module located in the cabinet; and
a heating unit that is located in the cabinet, that is coupled to the Peltier module, and that is configured to heat air flowing towards the holder air hole.

3. The clothes-treating apparatus of claim 2, further comprising:
a steam generator located in the cabinet and configured to generate steam,
wherein the holder further defines a holder steam hole configured to supply steam to the clothes hung on the holder.

4. The clothes-treating apparatus of claim 1, wherein the cabinet further defines an upper exhaust hole positioned at the upper panel and configured to supply heated air or unheated air to the clothes hung on the holder.

5. The clothes-treating apparatus of claim 1, further comprising:
an iron panel rotatably coupled to a front panel of the cabinet and configured to press the clothes towards the front panel of the cabinet.

6. The clothes-treating apparatus of claim 5, wherein the front panel of the cabinet defines a cabinet steam hole configured to spray steam toward the iron panel.

7. The clothes-treating apparatus of claim 6, wherein the front panel further defines a front exhaust hole configured to discharge heated air or unheated air.

8. The clothes-treating apparatus of claim 3, wherein the holder defines at least one of a holder air path configured to allow flow of air in the holder or a holder steam path configured to allow flow of steam in the holder.

9. The clothes-treating apparatus of claim 7, wherein the front panel of the cabinet defines at least one of (i) a front panel air path configured to allow flow of air in the front panel or (ii) a front panel steam path configured to allow flow of steam in the front panel.

10. The clothes-treating apparatus of claim 1, wherein the holder comprises:
   a first vertical member that extends in a vertical direction with respect to the upper panel of the cabinet;
   a second vertical member that extends in the vertical direction with respect to the upper panel of the cabinet and that is spaced apart from the first vertical member; and
   a connection member that connects an upper end of the first vertical member to an upper end of the second vertical member.

11. The clothes-treating apparatus of claim 10, wherein the connection member is inclined upward with respect to the first vertical member and the second vertical member.

12. The clothes-treating apparatus of claim 10, wherein the holder defines a plurality of holder air holes that are configured to supply air to the clothes hung on the holder, that are spaced apart from one another, and that are arranged along at least one of the first vertical member, the second vertical member, or the connection member.

13. The clothes-treating apparatus of claim 12, wherein the holder further defines a plurality of holder steam holes that are configured to supply steam to the clothes hung on the holder, that are spaced apart from one another, and that are arranged along at least one of the first vertical member, the second vertical member, or the connection member.

14. The clothes-treating apparatus of claim 13, wherein the plurality of holder air holes are positioned outward of the plurality of holder steam holes at the first vertical member, the second vertical member, and the connection member.

15. The clothes-treating apparatus of claim 13, wherein the holder further defines:
   a holder air path that is configured to allow flow of air along the first vertical member, the connection member, and the second vertical member; and
   a holder steam path that is configured to allow flow of steam along the first vertical member, the connection member, and the second vertical member, and
   wherein the plurality of holder air holes are arranged in the holder air path, and the plurality of holder steam holes are arranged in the holder steam path.

16. The clothes-treating apparatus of claim 15, wherein the holder air path is parallel to the holder steam path and configured to allow flow of air in a first direction along the first vertical member, the connection member, and the second vertical member, and
   wherein the holder steam path is configured to allow flow of steam in a second direction opposite to the first direction along the second vertical member, the connection member, and the first vertical member.

17. The clothes-treating apparatus of claim 10, wherein the cabinet further comprises a front panel that defines a front panel air path configured to allow flow of air in the front panel and that defines a front panel steam path configured to allow flow of steam in the front panel.

18. The clothes-treating apparatus of claim 17, further comprising:
   an air connection path that connects the front panel air path to one of the first vertical member or the second vertical member the holder; and
   a steam connection path that connects the front panel steam path to one of the first vertical member or the second vertical member the holder.

19. The clothes-treating apparatus of claim 1, wherein the air flow unit comprises one or more fans located between the holder and the rear panel and configured to cause air to be suctioned from the outside of the cabinet through the one or more suction holes.

20. A clothes-treating apparatus comprising:
   a cabinet comprising an upper panel that defines a holder opening;
   an air flow unit located in the cabinet and configured to generate air flow;
   a holder configured to insert into the cabinet through the holder opening and configured to hang clothes thereon; and
   an iron panel rotatably coupled to a front panel of the cabinet and configured to press the clothes towards the front panel of the cabinet,
   wherein the holder defines a holder air hole configured to supply air to the clothes hung on the holder.

* * * * *